United States Patent [19]

Scheiner

[11] Patent Number: 5,627,611

[45] Date of Patent: May 6, 1997

[54] ARTIFICIAL TEARS

[76] Inventor: Stanley A. Scheiner, P.O. Box 64109, Miami, Fla. 33164

[21] Appl. No.: 581,458

[22] Filed: Dec. 29, 1995

[51] Int. Cl.$^6$ .............................. G02C 1/00; G02C 11/08; A61M 35/00
[52] U.S. Cl. .............................. 351/158; 351/62; 604/300
[58] Field of Search ...................... 351/158, 62; 604/294, 604/300; 128/204.13

[56] References Cited

U.S. PATENT DOCUMENTS 4,908,024  3/1990  Py ........................................ 351/158 X

*Primary Examiner*—Huy Mai
*Attorney, Agent, or Firm*—Robert M. Schwartz

[57] ABSTRACT

A passive mechanism supplies moisture into a chamber formed by an eyeglass frame closely fitted over at least one eyeball and the adjacent cheek or cheeks of an eyeglass wearer. The moisture may be composed of water or any suitable evaporable eye drop fluid absorbed within a moisture absorbing member, such as cotton. A moisture pervious cover, such as a perforated cover or a fluid pervious cover is provided for the moisture-absorbing member. Moisture absorbed in the moisture absorbing member is evaporated through the cover into the chamber to increase the humidity within the chamber and counteract the discomfort and ocular damage that affects the eyeballs, particularly when the wearer is elderly. This invention replaces the previous need for frequent manual application of eye drops and provides a simple mechanism free of fluid pumping elements previously needed to supply fluid to the surface of the eyeballs. The frame may be vented to prevent fogging of lenses when the chamber becomes subject to hyper-humidity.

15 Claims, 2 Drawing Sheets

ARTIFICIAL TEARS

BACKGROUND OF THE INVENTION

1. Field of the Invention

This invention relates to devices for applying fluid to biological tissue and more particularly to apparatus which instills an aqueous solution to the surface of the eyeballs. The invention introduces artificial tear fluid to relieve the discomfort and potential ocular damage caused by chronic dry-eye condition, which is especially uncomfortable in elderly people. The invention also provides a corresponding method to treat eye dryness.

Many people suffer from a lack of eye moisture. Even though artificial tear solutions increase eye moisture and relieve discomfort, the application of such artificial tear solutions provides only temporary relief and therefore dry-eye sufferers commonly apply artificial tear solution to their eyes several times within the course of a day. The burden and interruption caused by frequent applications of eye drops is not conducive to maintain a proper moisture level and to apply the required dosages.

The present invention also finds use in applying an active medicinal agent dissolved in a volume of fluid administered to the eye. Fluids with active medical ingredients require careful control of the quantity of fluid administered. It generally is difficult, with manual application of the fluid using an eyedropper, to control the number of drops introduced to the eye.

Some eyedroppers exist with a fluid chamber having a threaded piston that screws within a correspondingly threaded cylinder. When the piston is advanced within the cylinder and held in a particular position, a predetermined volume of fluid is expelled from the chamber. However, due to the complicated structure of these devices, their bulkiness make them more cumbersome than typical eyedroppers.

Other devices have been developed to deliver fluid to an eyeball. These devices typically work by pumping fluid from a reservoir through a tube that has a distal end positioned adjacent to the eye. In some instances, the tube is surgically implanted under the skin. It begins at a fluid reservoir positioned, for example, at the lumbar region and ends adjacent the eye. These devices are cumbersome and invasive and the mechanism needed to pump the fluid through the tube is bulky and requires a heavy and bulky power source. Furthermore, control problems result from having to pump fluid to the eye through a relatively lengthy tube. Furthermore, fluid flow can easily be disrupted by patient movement and by inadvertent pinching or collapsing of the delivery tube.

In summary, the prior art has been characterized by apparatus that applies fluid droplets at a rapid and nonuniform localized flow so that such treatment/characteristic of the prior art causes non-uniform flooding on the exposed eyeball with damage to the eyeball resulting from the rapid, non-uniform application of moisture to the dry eyeball requiring treatment.

2. State of the Prior Art

U.S. Pat. No. 2,527,947 to Loos, issued Oct. 31, 1950, discloses a laminated eye protector comprising a flexible multiple ply pad consisting of an outer layer of relatively thick fabric which is relatively impervious to sun rays and moisture and is heat absorptive, an intermediate layer of absorbent material and an inner layer of relatively loosely woven fabric. The inner layer is porous to permit medication or water in the intermediate layer to travel through the inner layer to the eyeball surface. This patented device does not evaporate eye protecting moisture into a chamber immediately outside and surrounding the eyeball.

U.S. Pat. No. 3,826,258 to Abraham, issued Jul. 30, 1974, shows eye treatment apparatus that comprises a very small number of gradually released medicine carriers in a saline or antiseptic solution. The invention defined in this patent discloses a prepackaged ampoule-like dropper and does not provide means for evaporating an eye treating fluid within a chamber formed between an eyeglass frame on one hand and the eye and cheek of a user on the other hand.

U.S. Pat. No. 3,902,486 to Guichard, issued Sep. 2, 1975, relates to a portable nasal diffuser and is mentioned because this patent was reported in a novelty search. It would not be obvious to use a portable nasal diffuser to apply moisture to a dry eyeball surface.

U.S. Pat. No. 4,573,982 to Forbes, et al., issued Mar. 4, 1986, discloses an eyeglass frame constructed and arranged to apply a unit dose ophthalmic drug in liquid form. The liquid is applied directly to the eye as discrete droplets that treat the eyeball surface non-uniformly. A portion of the eyeball so treated remains dry after such treatment so that the dry eyeball problem is not fully corrected.

U.S. Pat. No. 4,908,024 to Py, issued Mar. 13, 1990, discloses an ocular treatment apparatus that is formed by a frame worn by a patient to support one or two light-deviation apparatus. The patient rotates his eyes upward and the light-deviation apparatus permits him to observe the lower ocular area to apply ocular treatment material in a location normally not seen by the wearer.

U.S. Pat. No. 5,171,306 to Vo, issued Dec. 15, 1992, discloses an eye drop delivery system for administering eye drops to at least one eye of a user and comprises a fluid reservoir for holding a supply of eye drop fluid, a tube for conducting eye drop fluid from the fluid reservoir to at least one eye of the user and fluid driving apparatus for continuously urging eye drop fluid from the fluid reservoir to at least one distal end of the tube and fluid control apparatus for successfully permitting eye drop fluid to flow freely from the tube. The fluid control means causes individual drops of eye drop fluid to be applied to the eye of the wearer.

U.S. Pat. No. 5,368,582 to Batera, issued Nov. 29, 1994, discloses a spectacle-like device that mounts a system of pump elements that can project droplets of liquid onto a wearer's eye. The use of pump elements complicates the structure of the device and does not suggest the slow, uniform application of evaporated fluid into a chamber adjacent to and surrounding the eyeballs.

BRIEF DESCRIPTION OF THE INVENTION

The present invention provides means for providing a "dead space" in front of the eyes. Moisture absorbed by a moisture absorbing material such as a cotton plug carried by a fluid impervious eyeglass frame is evaporated and released through a fluid pervious surface of a hollow frame when evaporated from the absorbent material or through apertures in an apertured cartridge reservoir fitted to the inside structure of a spectacle frame or within a slide-on passive reservoir attached to the temple of the spectacle frame.

The constant passive evaporation of the eye treating fluid from the absorbent material reservoir supported directly within the spectacle frame or on a replaceable apertured cartridge reservoir fitted to the spectacle frame causes the environment in contact with the eye to develop a high humidity environment of fluid moving more slowly than prior art devices to which the eyeballs are exposed. This slow fluid flow in the so-called "dead space" in front of a person's eyes counteracts the tendency of the eyeballs to become dry in response to the flow of air that is of relatively low humidity in contact with the outer surface of the eyeballs.

The present invention applies moisture to the surfaces of the eyeballs by a slower, more uniform and constant flow of evaporated moisture rather than pulses of pumped moisture or discrete drops applied to spaced areas of the eyeballs undergoing treatment of dry eye.

BRIEF DESCRIPTION OF THE DRAWINGS

In the drawings that form part of the description of preferred embodiments of this invention.

DESCRIPTION OF PREFERRED EMBODIMENT

The drawings depict various illustrative embodiments of this invention.

Figure 1:
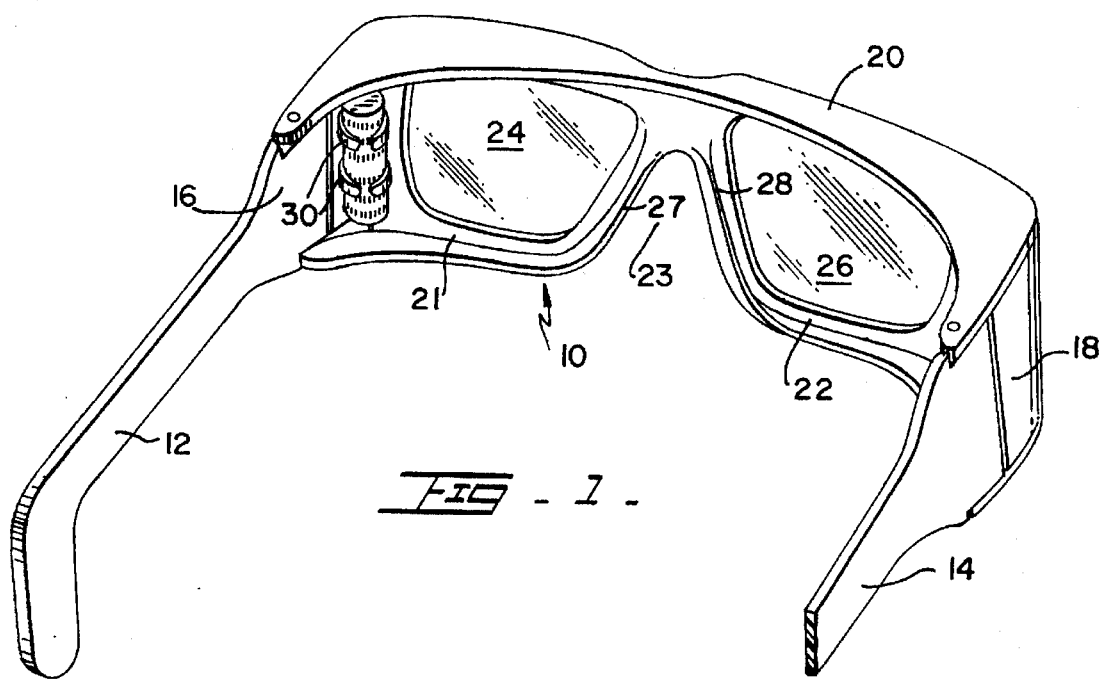
FIG. 1 is a fragmentary perspective view of a first embodiment of an eyeglass frame showing how a fluid absorbing member in the form of a porous plug may be supported by an eyeglass frame for storing said fluid within a cylinder which is removably attached to interior surface portions of said frame, which interior surface portions are apertured to permit evaporated liquid to be delivered through said apertures into a so-called "dead space" chamber formed between the eyeglass frame on one hand and the eyes and cheeks of a wearer on the other hand.
Figure 2:
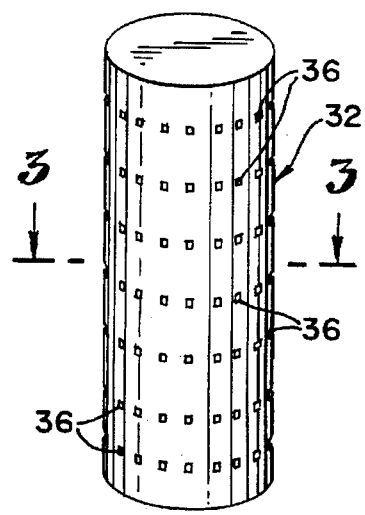
FIG. 2 is a perspective view of a plug storing cartridge that is apertured to permit a constant low pressure outflow of evaporated fluid into the "dead space" chamber and is included in the eye treatment embodiment of FIG. 1.
Figure 3:
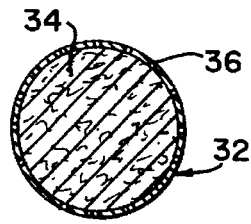
FIG. 3 is a cross-section view taken along the line 3—3 of FIG. 2.

Referring to the drawings, FIGS. 1, 2 and 3 show an eyeglass frame 10 having a left temple 12 and a portion of a right temple 14. Left temple 12 widens to form an enlarged left front temple portion 16 and right temple 14 enlarges to form an enlarged right front temple portion 18 seen in FIG. 1.

Eyeglass frame 10 forms a substantially horizontal front roof portion 20 and substantially horizontal lower lens holding portion comprising subportions 21 and 22 which latter are separated to form a nose opening 23 to separate the lower lens holding portion into two subportions 21 and 22 that support left lens 24 and right lens 26, respectively. Nose opening 23 extends generally in a vertical plane and includes a pair of diverging lens holding portions 27 and 28 which extend downward from roof portion 20 toward the bottom lens holding subportions 21 and 22.

The inner end of the horizontally extending front roof portion 20 is arranged to conform to the shape of the forehead of a wearer of the eyeglass frame 10. Thus the front roof portion 20 serves as a roof of a so-called "dead space" chamber and the lens holding portions 21 and 22 cooperate with lenses 24 and 26 to serve as a vertical front wall of the "dead space" chamber. The nose of the wearer fits into the recess of nose opening 23 and the enlarged left and right front portions 16 and 18 of left temple 12 and right temple 14, respectively, cooperate with the cheek and eyes of the wearer to provide side walls for the chamber within which a relatively stagnant atmosphere is located.

The inner surface of enlarged left front portion 16 and enlarged right front portion 18 support a plurality of vertically aligned sets of flexible clips 30 which are readily distorted to receive an apertured cartridge 32 at each front inner corner of the eyeglass frame 10. The apertured cartridges 32 are filled with a plug 34 of fluid absorbent material such as a cotton plug. Apertures 36 in the walls of the apertured cartridge 32 provide passageways for the removal of evaporated water or other liquid from the plug 34 of fluid absorbent material into the chamber formed between the upper face and eye portions of the wearer and the eyeglass frame 10.

In the first embodiment of FIGS. 1, 2 and 3, apertured cartridges 32 are insertable in a set of vertically aligned clips 30 near each front corner of the eyeglass frame 10 to provide ready insertion into each set of clips 30 of an apertured cartridge 32, each containing a different plug 34 of fluid absorbent material. Moisture absorbed within the plug 34 is gradually evaporated over a period of time without requiring any pumping means and the evaporated fluid escapes through apertures 36 of the apertured cartridges 32 into the chamber formed between the eyeglass frame 10 and the face and eyes of the wearer. The bottom lens holding subportions 21, 22 are of arcuate shape so that they form the bottom of the chamber between the eyeglass frame 10 and the portion of the face of the wearer that includes the wearer's eyes.

Figure 4:
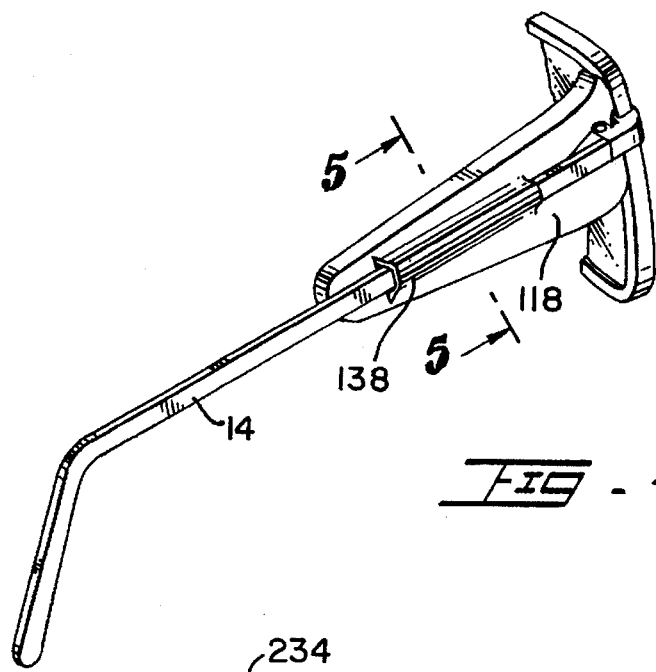
FIG. 4 is a side view of an eyeglass frame showing an alternate embodiment of this invention wherein the moisture absorbing member forms a side barrier so that the moisture absorbed within the moisture absorbing medium such as the cotton plug may be evaporated through a series of apertures in a side wall of the eyeglass frame that face said "dead space" chamber.
Figure 5:
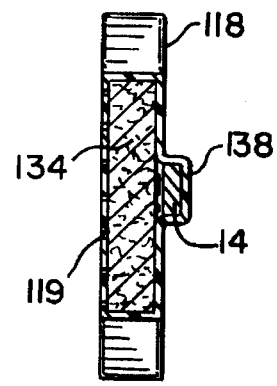
FIG. 5 is a cross-section view taken along the line 5—5 of FIG. 4.
Figure 6:
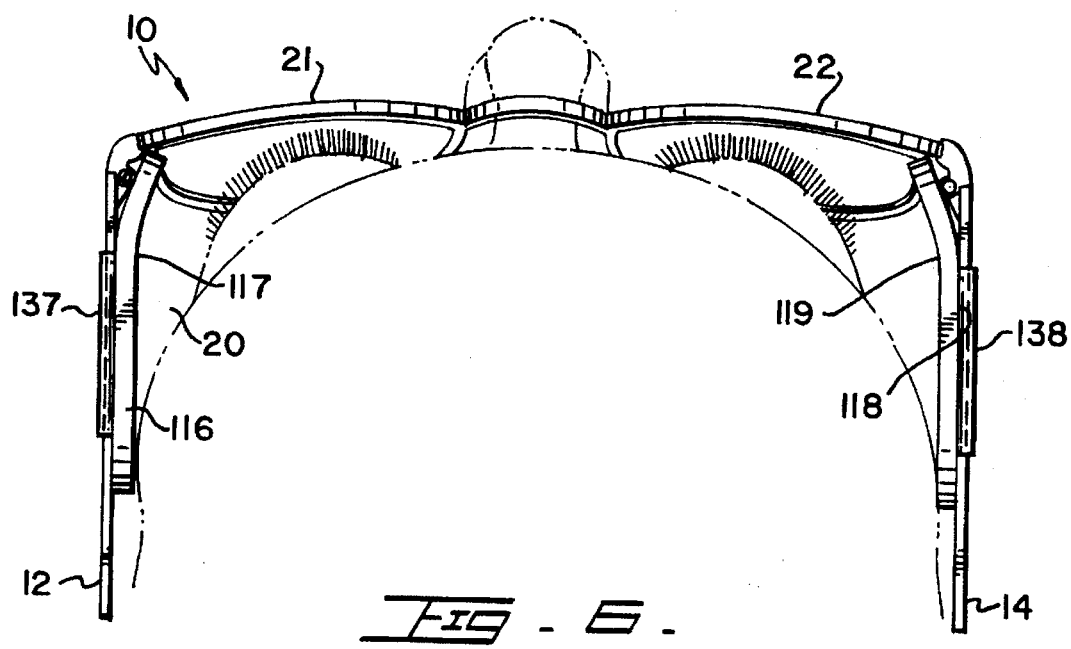
FIG. 6 is a top view of the eyeglass frame of FIGS. 4 and 5.

Referring to FIGS. 4, 5 and 6, it is noted that a left temple 112 extends alongside an enlarged left front portion 116 and a right temple 114 extends alongside an enlarged right front portion 118 of the frame. Enlarged portions 116 and 118 have fluid pervious inner surfaces 117 and 119, respectively that serve the same purpose as apertures 36 of apertured cartridges 32 facing inward toward the "dead space" chamber of the embodiment of FIGS. 1, 2 and 3. Large front portions 116 and 118 are shown as hollow with the interior facing fluid pervious surfaces of the hollow large front portions 116 and 118 serving the purpose of apertures 36 of cartridges 32 of the first embodiment. In addition, plugs 134 of fluid absorbent material within hollow large front portions 116 and 118 serve the same purpose as plugs 34 of the first embodiment, and apertures 136 of the FIGS. 4, 5 and 6 embodiment serve the same purpose as the inwardly facing apertures 36 of the first embodiment. Left temple 12 extends through a tunnel 137 exteriorly of enlarged left front portion 116 of left temple 12 and a tunnel 138 is attached to the exterior surface of enlarged right front portion 118 of temple 14 so that left temple 12 extends through left tunnel 137 and right temple 14 extends through right tunnel 138.

Figure 7:
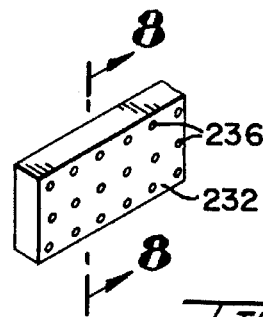
FIG. 7 is a perspective view of a third embodiment wherein the inner walls of the opposite temples are hollow and have fluid pervious inner walls to permit ocular treatment fluid to seep into the so-called "dead space" chamber behind the lenses of the eyeglass frame from a moisture-impregnated member within the hollow temples.
Figure 8:
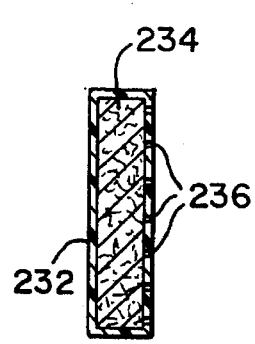
FIG. 8 is a sectional view taken along the line 8—8 of FIG. 7.

In the embodiment of FIGS. 7 and 8, a hollow body 232 serves the purpose of apertured cartridge 32 of the first embodiment or hollow cartridge 132 of the second embodiment and a plug 234 filled with fluid absorbent material contains fluid which evaporates and escapes as a slow gentle fluid flow through apertures 236 to increase the humidity within the atmosphere or environment in the "dead space" chamber between the eyes and face of the wearer on one hand and the eyeglass frame on the other hand.

The frame of any of the foregoing embodiments may be vented by applying vent holes to any wall of the frame facing away from the "dead air" space chamber when necessitated by hyper-humidity within the chamber. Under such circumstances, the vent holes prevent fogging of the lenses.

Conforming to the provisions of the patent statutes, applicant has provided an explanation of the principle, preferred construction and mode of operation of this invention and has illustrated and described what is now considered to be its best embodiments. It is understood, however, that within the scope of the claimed subject matter that follows, the invention may be set forth otherwise than as specifically illustrated and described in this specification.

What is claimed is:

1. Apparatus for use with an eyeglass frame that is constructed and arranged to define a chamber in front of at least one eyeball of a wearer of said eyeglass frame to reduce the rate at which an exposed surface of said eyeball of a wearer becomes dry, comprising a plug of moisture absorbent material containing evaporable moisture therein carried by said frame, means to cover said plug and to provide at least one path through said cover means in a direction toward said chamber to increase the humidity of said chamber between said frame and said eyeball surface without requiring any pumping action to deliver said moisture to said chamber.

2. Apparatus as in claim 1, wherein said eyeglass frame has a pair of temples, each having an enlarged front portion forming enlarged front side wall portions of said chamber, a roof portion conforming in shape to the forehead of said wearer to form the roof of said chamber and lens holding portions constructed and arranged to conform to the cheeks of said wearer to form a floor for said chamber.

3. Apparatus as in claim 1, including flexible clip means carried by said eyeglass frame, wherein said plug covering means comprises an apertured cartridge constructed and arranged to be readily attached and/or removed from said flexible clip means carried by said eyeglass frame.

4. Apparatus as in claim 1, wherein said eyeglass frame comprises a pair of temples, a tunnel carried by each temple, an internally extending apertured wall for each tunnel and said plug of moisture absorbent material carried by each said tunnel for delivery of absorbed moisture by evaporation through said apertured wall into said chamber.

5. Apparatus as in claim 4, wherein each said temple is hollow to receive a plug of moisture absorbent material and each said temple has an apertured inner wall facing said chamber through which moisture is evaporated from said plug into said chamber without requiring any pumping action.

6. Apparatus as in claim 1, further including vent holes for said frame constructed and arranged to prevent fogging of lenses carried by said frame, under hyper-humidity conditions.

7. Apparatus for controlling the dryness of an eyeball of a wearer of an eyeglass frame constructed and arranged to form a chamber in front of the eyes of a wearer of said eyeglass frame and behind said frame, said eyeglass frame constructed and arranged to support at least a pair of plugs of moisture absorbing material impregnated with moisture and means to support said plugs within said frame, said support means being constructed and arranged to provide passage for moisture evaporated from said plugs into said chamber.

8. Apparatus as in claim 7, wherein said plug support means comprises an apertured cartridge having apertures constructed and arranged to deliver evaporated moisture from said moisture impregnated plugs into said chamber without requiring any pumping action.

9. Apparatus as in claim 7, wherein said eyeglass frame comprises a pair of hollow temples in which said plugs are stored, each of said temples having an inner apertured wall providing a series of apertures for delivering moisture evaporated from said plugs into said chamber without requiring any pumping action.

10. Apparatus as in claim 9, wherein said hollow temples each have outwardly facing solid walls supporting a tunnel for receiving a corresponding temple and a relatively wide portion of hollow construction for supporting said plugs in said relatively wide portions, each of said relatively wide portions having an inner apertured wall providing passage for said moisture into said chamber when the latter is evaporated from said plugs.

11. Apparatus as in claim 7, wherein said eyeglass frame is constructed and arranged to have a roof portion corresponding in shape to the shape of the forehead of a wearer of said eyeglass frame and a lens supporting bottom portion corresponding in shape to the shape of the cheeks of said wearer.

12. A method of controlling the dryness of the exposed surface of an eyeball comprising causing a patient suffering from eyeball dryness to wear an eyeglass frame supporting a plug of moisture absorbing material having moisture absorbed therein in such a manner that the frame is spaced from said patient to form a chamber in front of the eyes of said patient, and delivering moisture evaporated at an evaporation rate sufficient to moisten the eyeball but insufficient for said delivered moisture to harm said exposed eyeball surface from said plug into said chamber through moisture pervious portions of said eyeglass frame.

13. A method as in claim 12, wherein said evaporated moisture from said plug is delivered into said chamber through apertures extending through inner walls of said frame.

14. A method as in claim 12, wherein said evaporated moisture from said plug is delivered into said chamber through a fluid pervious wall of said frame.

15. A method as in claim 12, further including venting a sufficient portion of said evaporated moisture away from said frame and said chamber in such a manner as to prevent fogging of any lens carried by said frame under hyper-humidity conditions.

* * * * *